(12) United States Patent
Lin et al.

(10) Patent No.: US 11,994,450 B2
(45) Date of Patent: May 28, 2024

(54) FIELD SURVEYING AND REGULATING SYSTEM AND METHOD

(71) Applicant: FOXSEMICON INTEGRATED TECHNOLOGY, INC., Miao-Li Hsien (TW)

(72) Inventors: Ching-Wen Lin, Miaoli Hsien (TW); Wei-Chen Su, Miaoli Hsien (TW)

(73) Assignee: FOXSEMICON INTEGRATED TECHNOLOGY, INC., Miao-Li Hsien (TW)

( * ) Notice: Subject to any disclaimer, the term of this patent is extended or adjusted under 35 U.S.C. 154(b) by 440 days.

(21) Appl. No.: 17/369,832

(22) Filed: Jul. 7, 2021

(65) Prior Publication Data
US 2022/0050025 A1 Feb. 17, 2022

(30) Foreign Application Priority Data
Aug. 14, 2020 (CN) .......................... 202010820504.3

(51) Int. Cl.
| | |
|---|---|
| *G06Q 10/00* | (2023.01) |
| *G01C 15/02* | (2006.01) |
| *G01N 1/08* | (2006.01) |
| *G01N 33/24* | (2006.01) |

(Continued)

(52) U.S. Cl.
CPC .............. *G01N 1/08* (2013.01); *G01C 15/02* (2013.01); *G01N 33/24* (2013.01); *G06Q 10/06395* (2013.01); *G01N 2001/021* (2013.01)

(58) Field of Classification Search
None
See application file for complete search history.

(56) References Cited

U.S. PATENT DOCUMENTS

| | | | | |
|---|---|---|---|---|
| 6,199,000 | B1 * | 3/2001 | Keller ................. | A01B 79/005 342/357.62 |
| 6,516,271 | B2 * | 2/2003 | Upadhyaya .......... | A01C 21/005 56/10.2 A |
| 9,103,195 | B2 * | 8/2015 | Gawski ................. | E21B 44/04 |

(Continued)

FOREIGN PATENT DOCUMENTS

| | | |
|---|---|---|
| CN | 104871458 B | 12/2016 |
| TW | 201128554 A1 | 8/2011 |

OTHER PUBLICATIONS

A Sakamoto, H Fukui et al. (Development and application of a livable environment evaluation support system using Web GIS) Journal of Geographical Systems, 2004—Springer. (Year: 2004).*

(Continued)

*Primary Examiner* — Hafiz A Kassim
(74) *Attorney, Agent, or Firm* — ScienBiziP, P.C.

(57) ABSTRACT

A field surveying and regulating method applied on at least one monitoring electronic device enables at least one manager to add at least one project and at least one specific location (spot) for obtaining soil samples and to edit the at least one project and the at least one spot on an online map. The method allows the manager to assign at least one soil drill and at least one drill operator for each project and each spot. The method enables the manager to view information as to position of each soil drill, depth for sampling by each soil drill, sampling time spent, actual work done by each soil drill, and photos of work by each soil drill in sampling. A related field surveying and regulating system is also disclosed.

15 Claims, 6 Drawing Sheets

(51) Int. Cl.
*G06Q 10/0639* (2023.01)
*G01N 1/02* (2006.01)

(56) References Cited

U.S. PATENT DOCUMENTS

| | | | |
|---|---|---|---|
| 9,388,680 B2 * | 7/2016 | Moran | E21B 44/00 |
| 10,255,670 B1 * | 4/2019 | Wu | H04N 7/183 |
| 2008/0091496 A1 * | 4/2008 | Gurpinar | G06Q 10/06 |
| | | | 705/7.28 |
| 2014/0006074 A1 * | 1/2014 | Cockburn | E02F 9/261 |
| | | | 705/7.11 |
| 2015/0094916 A1 * | 4/2015 | Bauerer | A01C 7/128 |
| | | | 701/50 |
| 2015/0229439 A1 | 8/2015 | Stolpman et al. | |
| 2017/0041407 A1 * | 2/2017 | Wilbur | G06Q 50/02 |
| 2020/0128721 A1 * | 4/2020 | Lewis | A01B 79/02 |
| 2022/0279704 A1 * | 9/2022 | Sharda | G05B 19/4155 |

OTHER PUBLICATIONS

SK Nielsen, LJ Munkholm, M Lamandé (Seed drill depth control system for precision seeding) electronics in . . . , 2018—Elsevier (Year: 2018).*

Q Wang, Q Zhang, F Rovira-Más, L Tian (Stereovision-based lateral offset measurement for vehicle navigation in cultivated stubble fields) Biosystems engineering, 2011—Elsevier (Year: 2011).*

RJ Godwin, PCH Miller (A review of the technologies for mapping within-field variability) Biosystems engineering, 2003—Elsevier (Year: 2003).*

* cited by examiner

FIELD SURVEYING AND REGULATING SYSTEM AND METHOD

FIELD

The subject matter herein generally relates to agricultural technology and particularly, to a field surveying and regulating system and a field surveying and regulating method.

BACKGROUND

In studying soils, drill operators employ tools, for example, a tapeline, a GPS device, a theodolite, a level, and so on, and determine a detailed position of a sampling point on the site, using a recorder to record results and transmit the recorded result to a manager for his statistics and collections and do an instruction accordingly. However, the work by the drill operators consumes a lot of manpower and time, and the likelihood of errors become greater the greater the amount of data collected. Also, the manager is not on site, and cannot know an actual rate of progress of work as the work is being done, thus there may be a nonconformity with actual data on site, and ineffective regulation of the field or other area of soil may be the result.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure. Moreover, in the drawings, like reference numerals designate corresponding parts throughout the several views.

DETAILED DESCRIPTION

Figure 1:
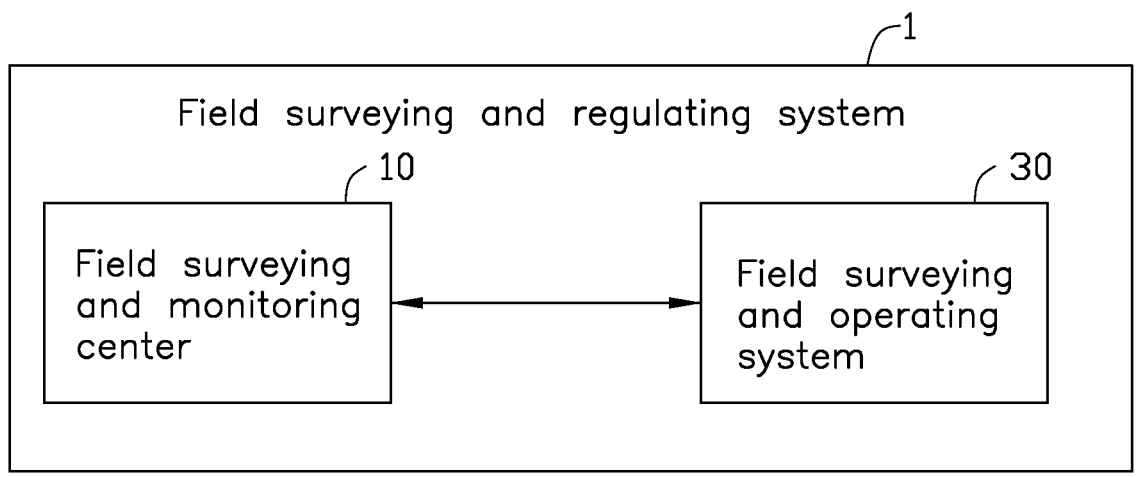
FIG. 1 illustrates a block diagram of an embodiment of a field surveying and regulating system.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The present disclosure, referencing the accompanying drawings, is illustrated by way of examples and not by way of limitation. It should be noted that references to "an" or "one" embodiment in this disclosure are not necessarily to the same embodiment, and such references mean "at least one."

FIG. 1 illustrates a block diagram of an embodiment of a field surveying and regulating system 1. The field surveying and regulating system 1 provides to a manager a project plan, an overview by way of monitoring, and an overall management role, and provides one or more drill operators each with a task on site, a sampling and positioning role, a data storage capacity, and a work return. The field surveying and regulating system 1 includes a field surveying and monitoring center 10 and a field surveying and operating system 30. The field surveying and monitoring center 10 provides monitoring on site for the manager. The field surveying and monitoring center 10 is applied on a monitoring electronic device. The field surveying and operating system 30 and the field surveying and monitoring center 10 communicate with each other. The field surveying and operating system 30 provides project information and spot information to the drill operators on site, as assigned by the manager. The field surveying and operating system 30 is applied on an operating electronic device. One or more monitoring electronic devices for monitoring purposes (monitoring electronic devices) and one or more operating electronic devices in the hands of the drill operators constitute the field surveying and regulating system 1. The one or more monitoring electronic devices can communicate with the one or more operating electronic devices.

Figure 2:
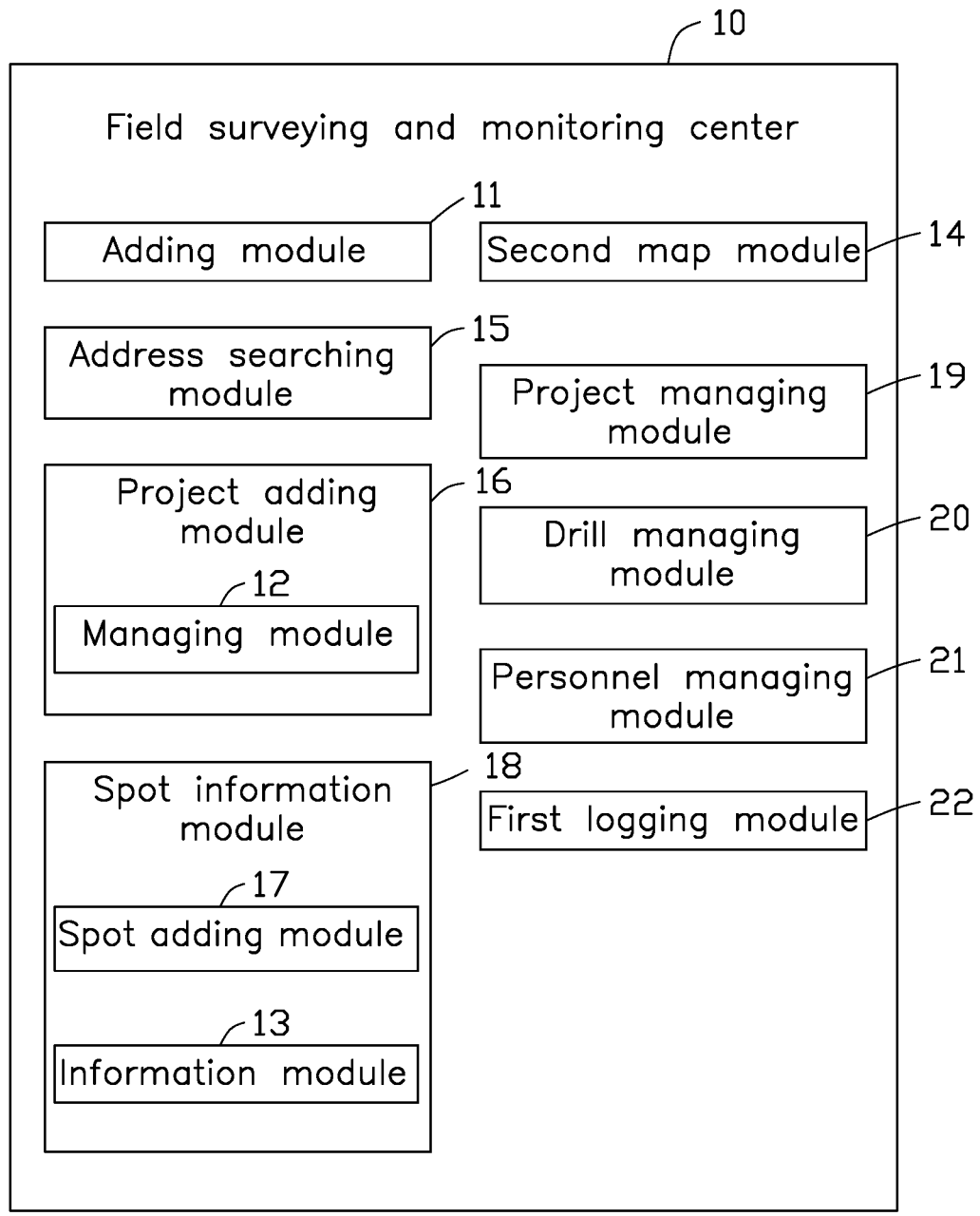
FIG. 2 illustrates a block diagram of an embodiment of a field surveying and monitoring center.
Figure 3:
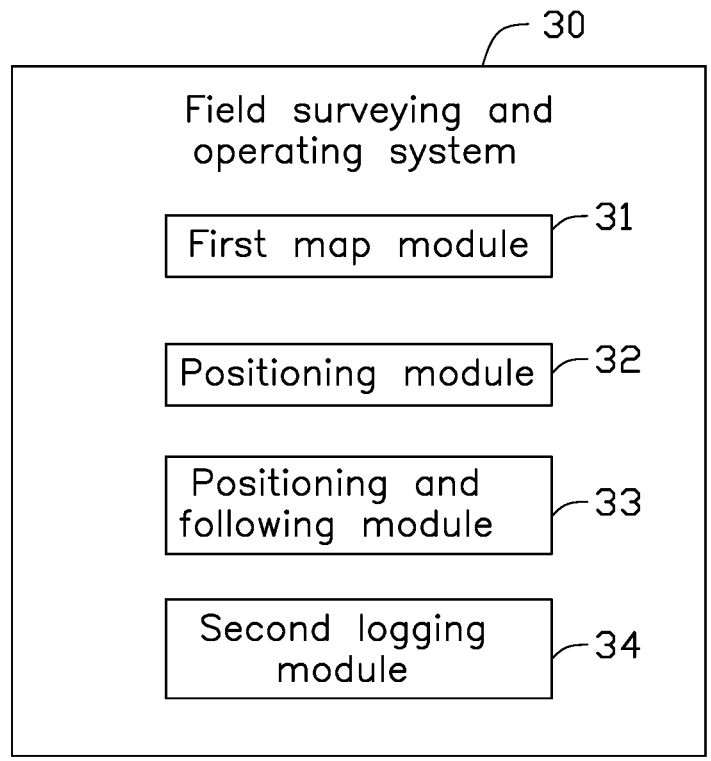
FIG. 3 illustrates a block diagram of an embodiment of a field surveying and operating system.

Referring to FIGS. 2-3, FIG. 2 illustrates a block diagram of an embodiment of a field surveying and monitoring center, and FIG. 3 illustrates a block diagram of an embodiment of a field surveying and operating system. The field surveying and monitoring center 10 includes an adding module 11, a managing module 12, and an information module 13. The adding module 11 allows the manager to add one or more projects and information as to one or more spots, and to edit the projects and the spot information on an online map. The managing module 12 enables the manager to assign one or more soil drills and one or more drill operators for each project and each spot of which they are given information. For convenience, only one soil drill and one drill operator is described below in detail, it being understood that more soil drills and more drill operators can be assigned. The information module 13 provides information for the manager to view regarding drill position of the soil, information as to drill depth, drill time spent sampling, actual work done by the soil drill, and one or more photos of actual drill-sampling. The field surveying and operating system 30 includes a first map module 31 and a positioning module 32. The first map module 31 provides a view for the drill operator of the project information of the projects of the online map and the spot information of the spots of the online map to determine information as to drilling for samples of the soil drill. The soil drill includes a real-time Kinematic (RTK) measuring machine. The positioning module 32 is configured to receive return information returned from the RTK measuring machine. The return information includes drill position of the soil, information as to drill depth, and drill time spent sampling. The positioning module 32 is further configured to receive input actual work done by the soil drill, and one or more input photos of actual drill-sampling, and transmit the returned drill position of the soil, the returned information as to drill depth, the returned drill time spent sampling, the input actual work done by the soil drill, and the input photos of actual drill-sampling to the field surveying and monitoring center 10.

The field surveying and monitoring center 10 further includes a second map module 14. The second map module 14 provides the online map. The online map includes an online electronic map, and an online surface-topography map. The second map module 14 is further configured to provide a switching option on the online map for switching between the online electronic map and the online surface-topography map. The adding module 11 includes an address searching module 15. The address searching module 15 provides an address-searching option for operating, provides a project input interface in response to a selection operation on the address-searching option, and receives a first address information input in the project input interface to provide for the manager to add the project on the online map. The address searching module 15 is further configured to provide a project interface for inputting a project name, a sampling date of the soil drill, information of the drill operator, information of the soil drill, and a sampling method of the soil drill, and so on. In the embodiment, the address searching module 15 is further configured to indicate and display the project on the online map with a first mark.

The adding module 11 further includes a project adding module 16. The project adding module 16 is configured to provide a project adding option, receive a selection operation on the project adding option, and receive a selection operation on the online map to add the project on the online map. The project adding module 16 includes the managing module 12. The managing module 12 is further configured to provide a project interface for inputting the project name, the sampling date of the soil drill, the information of the drill operator, the information of the soil drill, and the sampling method of the soil drill to assign the soil drill and the drill operator for each project and each spot. In the embodiment, the project adding module 16 is further configured to indicate and display the project on the online map with the first mark. The adding module 11 is further configured to provide a project editing option, and provide a project editing interface for inputting an editing of the project name, an editing of the sampling date of the soil drill, editing of the information of the drill operator, editing of the information of the soil drill, and an editing of the sampling method of the soil drill in response to a selection operation on the project editing option.

The adding module 11 further includes a spot adding module 17. The spot adding module 17 is configured to provide a first spot adding option to add a specific location for operating (first spot adding option), receive a selection operation on the first spot adding option, and receive one or more selection operations on the online map to add one or more spots on the online map. The spot adding module 17 is further configured to provide a spot input interface in response to a selection operation on the first spot adding option, and receive a second address information input in the spot input interface to provide for the manager to add a spot on the online map. In the embodiment, the spot adding module 17 is further configured to display the spots on the online map with a second mark.

The adding module 11 further includes a spot information module 18. The spot information module 18 is configured to provide information of all the spots (that is, all the specific locations) for viewing. The spot information module 18 is further configured to provide for the manager to add and edit the spots, and distribute spots via a grid distribution spot method. In detail, the spot information module 18 includes the spot adding module 17. The spot information module 18 is configured to provide the first spot adding option. The spot information module 18 is further configured to provide a grid distribution option for operating, expand a grid from a position of the project and provide a grid input interface in response to a selection operation on the grid distribution option, and receive a size of the grid and a scale of the grid input in the grid input interface to establish the grid. The spot information module 18 is further configured to provide a second spot adding option for operating, receive a selection operation on the second spot adding option, and receive one or more selection operations on the online map to add one or more spots on the online map. In the embodiment, the spot information module 18 is further configured to display the spots on the online map with the second mark. The spot information module 18 is further configured to provide an input interface in response to a selection operation on the second spot adding option, and receive a third address information input in the input interface to provide for the manager to add the spot on the online map. The spot information module 18 is further configured to provide a spot deletion option for each spot, and delete the spot corresponding to the spot deletion option in response to a selection operation on the spot deletion option. The spot information module 18 is further configured to provide a position editing option for each spot, provide a spot editing input interface in response to a selection operation on the position editing option, and receive a fourth address information input in the spot editing input interface to provide for the manager to edit position of the spot on the online map. The spot information module 18 is further configured to provide a spot information editing option for each spot, provide a spot information input interface in response to a selection operation on the spot information editing option, and receive an input in the spot information input interface to amend or edit the soil drill assigned for each spot, the drill operator assigned for each spot, a depth assigned for each spot, and a position assigned for each spot. The spot information module 18 further includes the information module 13. The information module 13 is configured to provide information option for each spot, and provide for the manager to view the drill position of the soil, information as to drill depth, drill time spent sampling, the actual work done by the soil drill, and the photos of actual drill-sampling in response to a selection operation on the information option.

The second map module 14 is further configured to provide for the manager to view the project information of the projects of the online map and the spot information of the spots of the online map on the online map in response to a selection operation on the first mark on the online map. The second map includes the spot information module 18. The second map further provides spot information option when providing the project information of the projects and the spot information of the spots. The spot information module 18 is configured to provide the information as to all spots for viewing in response to a selection operation on the spot information option.

The field surveying and monitoring center 10 further includes a project managing module 19, a drill managing module 20, and a personnel managing module 21. The project managing module 19 is configured to provide for the manager to edit the project information of the projects. The project information includes the project name, the sampling date of the soil drill, the ID and information of the drill operator, the information of the soil drill, the sampling method of the soil drill, and the time spent information of sampling by the soil drill. The drill managing module 20 is configured to add one or more soil drills, cancel one or more soil drills, edit types and descriptions of one or more soil drills, and edit work states of one or more soil drills for each project and each spot. The personnel managing module 21 is configured to add one or more drill operators for the projects, delete one or more drill operators for the projects, and edit names of one or more drill operators. In detail, the project managing module 19 is configured to provide a project managing option for operating, and provide for the manager to edit the project information of the project in response to a selection operation on the project managing option. The drill managing module 20 is configured to provide a drill managing option for operating, and provide for the manager to add the one or more soil drills, cancel the one or more soil drills, edit the types and descriptions of one or more soil drills, and edit the work states of one or more soil drills in response to a selection operation on the drill managing option. The personnel managing module 21 is configured to provide a personnel managing option for operating, and provide for the manager to add the one or more drill operators for the projects, delete the one or more drill operators for the projects, and edit the names of one or more drill operators.

The field surveying and operating system 30 further includes a positioning and following module 33. The positioning and following module 33 is configured to control the online map to track the soil drill and switch screen to display a position of latitude and longitude of the soil drill and a height of the soil drill in real time when performing a sampling process. In detail, the positioning and following module 33 is configured to provide a positioning and tracking option during operations, and control the online map to track the soil drill and switch the screen to display the latitude and the longitude of the soil drill and the current depth of the soil drill in real time in response to a selection operation on the positioning and tracking option when performing a sampling process.

In the embodiment, the field surveying and monitoring center 10 further includes a first logging module 22. The first logging module 22 provides a logging-in process for the manager to log into the field surveying and monitoring center 10. In detail, the first logging module 22 is configured to provide a first logging interface to provide for the manager to log into the field surveying and monitoring center 10. After the manager logs into the field surveying and monitoring center 10, the field surveying and monitoring center 10 provides the online map for viewing via the second map module 14, and provides a listing of function options including the address-searching option, a project adding option, a project managing option, a drill managing option, and a personnel managing option via the address searching module 15, the project adding module 16, the project managing module 19, the drill managing module 20, the personnel managing module 21. The field surveying and operating system 30 further includes a second logging module 34. The second logging module 34 is configured to provide a logging-in process for a drill operator to log into the field surveying and operating system 30. In detail, the second logging module 34 is configured to provide a second logging interface to provide for the drill operator to log into the field surveying and operating system 30. After the drill operator logs into the field surveying and operating system 30, the online map is provided for viewing via the first map module 31, and the positioning and tracking option on the online map is provided via the positioning and following module 33.

In the disclosure, the manager can do a project plan via the adding module 11 and the managing module 12 of the field surveying and monitoring center 10, the drill operator can receive the task and the sampling and the position, via the first map module 31 of the field surveying and operating system 30. The drill operator can submit a return of work done via the positioning module 32 of the field surveying and operating system 30, the manager can monitor the same via the information module 13 of the field surveying and monitoring center 10. Thus, the drill operator can determine the detail position of sampling point on site without tools, for example, the drill operator does not need the tapeline, the GPS device, the theodolite, and the level, and the operation efficiency and accuracy of the drill operator can be improved accordingly. The data obtained by the manager and the actual data on site are timely if not in real time and are linked, a nonconformity between the manager and the drill operator is avoided, and the likelihood of inappropriate regulation of the field is reduced.

Figure 4:
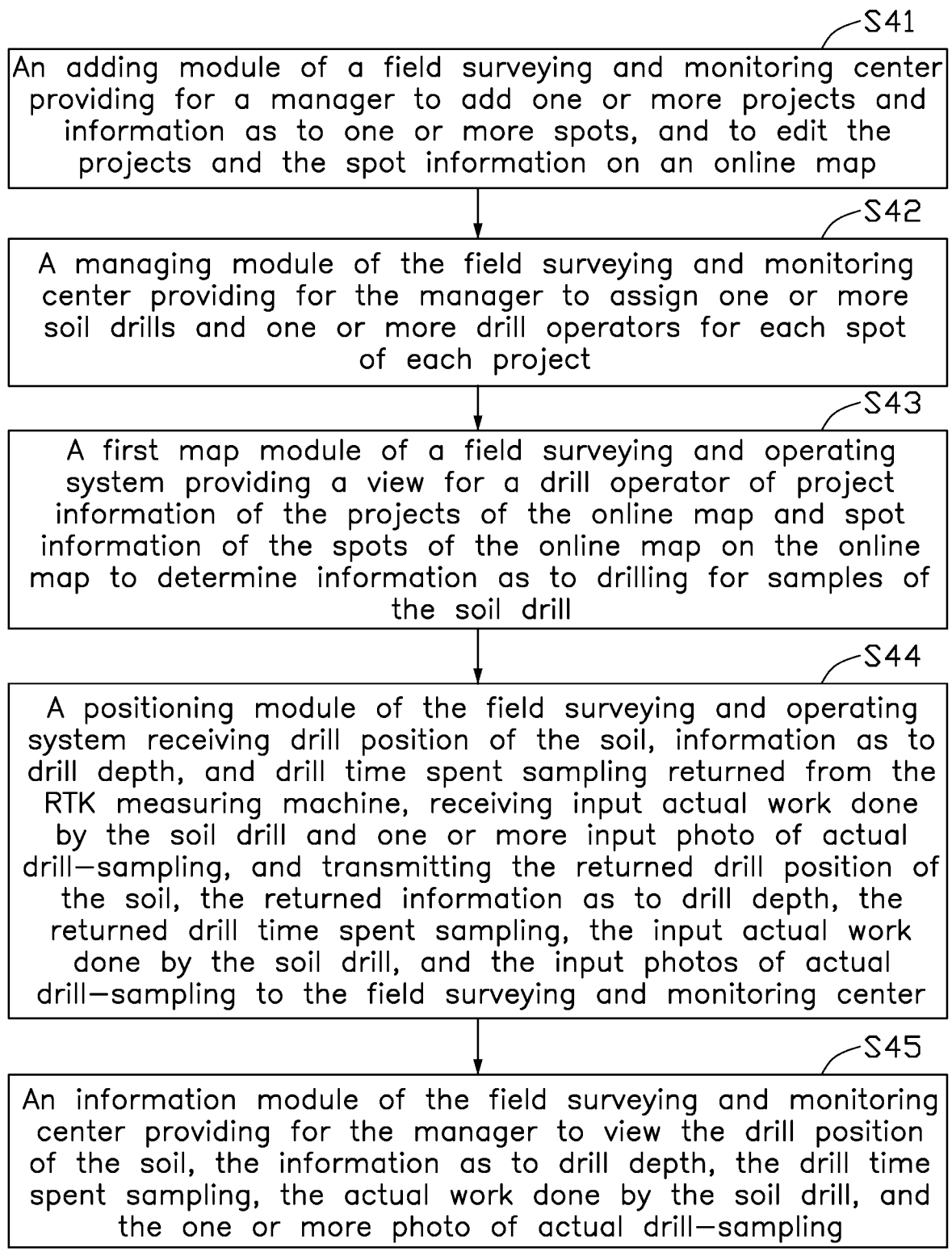
FIG. 4 illustrates a flowchart of a method in one embodiment for field surveying and regulating.

Referring to FIG. 4, FIG. 4 illustrates a flowchart of an embodiment of a method for field surveying and regulating. The method for field surveying and regulating can be applied on a field surveying and regulating system. Steps performed by a field surveying and monitoring center can be applied on a monitoring electronic device. Steps performed by a field surveying and operating system can be applied on an operating electronic device. The method can include the following:

At block S41, an adding module of the field surveying and monitoring center providing for a manager to add one or more projects and information as to one or more spots, and to edit the projects and the spot information on an online map.

At block S42, a managing module of the field surveying and monitoring center providing for the manager to assign one or more soil drills and one or more drill operators for each spot of each project.

At block S43, a first map module of the field surveying and operating system providing a view for a drill operator of project information of the projects of the online map and spot information of the spots of the online map on the online map to determine information as to drilling for samples of the soil drill, the soil drill including a real-time Kinematic (RTK) measuring machine.

At block S44, a positioning module of the field surveying and operating system receiving drill position of the soil, information as to drill depth, and drill time spent sampling returned from the RTK measuring machine, receiving input actual work done by the soil drill and one or more input photo of actual drill-sampling, and transmitting the returned drill position of the soil, the returned information as to drill depth, the returned drill time spent sampling, the input actual work done by the soil drill, and the input photos of actual drill-sampling to the field surveying and monitoring center.

At block S45, an information module of the field surveying and monitoring center providing for the manager to view the drill position of the soil, the information as to drill depth, the drill time spent sampling, the actual work done by the soil drill, and the one or more photo of actual drill-sampling.

In the embodiment, the method further includes a block a1. The block a1 includes a second map module of the field surveying and monitoring center providing the online map, and an address searching module of the adding module providing an address-searching option for operating, providing a project input interface in response to a selection operation on the address-searching option, and receive a first address information input in the project input interface to provide for the manager to add the project on the online map.

In the embodiment, the method further includes a block b1. The block b1 includes a spot adding module of the adding module providing a first spot adding option for operation, receiving a selection operation on the first spot adding option, and receiving one or more selection operations on the online map to add one or more spots on the online map.

In the embodiment, the method further includes a block c1. The block c1 includes a project managing module of the field surveying and monitoring center providing for the manager to edit the project information of the projects. The project information includes a project name, a sampling date of the soil drill, ID and information of the drill operator, information of the soil drill, a sampling method of the soil drill, and time spent information of sampling by the soil drill. The block c1 further includes a drill managing module of the field surveying and monitoring center adding one or more soil drills, cancelling one or more soil drills, editing types and descriptions of one or more soil drills, and editing work states of one or more soil drills for each project and each spot. The block c1 further includes a personnel managing module of the field surveying and monitoring center adding one or more drill operators for the projects, deleting one or more drill operators for the projects, and editing names of one or more drill operators for each project and each spot.

In the embodiment, the method further includes a block d1. The block d1 includes a positioning and following module of the field surveying and operating system controlling the online map to track the soil drill and switch screen to display a position of latitude and longitude of the soil drill and a height of the soil drill in real time when performing a sampling process.

The field surveying and regulating method can vary to another embodiments, the varied embodiments of the method are the same as the varied embodiments of the field surveying and regulating system, which are not described herein.

Figure 5:
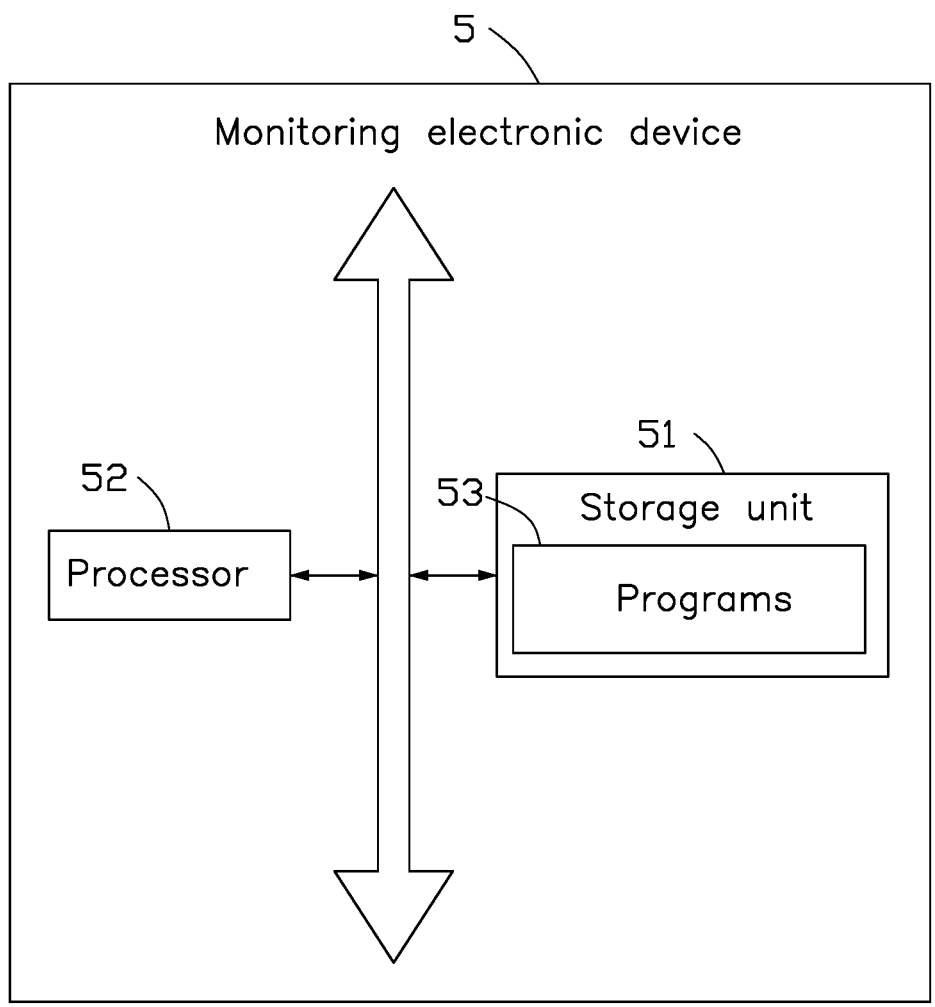
FIG. 5 illustrates a block diagram of an embodiment of a monitoring electronic device.

FIG. 5 illustrates a block diagram of an embodiment of a monitoring electronic device. The monitoring electronic device 5 can include a storage unit 51, at least one processor 52, and one or more programs 53 stored in the storage unit 51 which can be run on the at least one processor 52. The at least one processor 52 can execute the one or more programs 53 to accomplish the steps of the exemplary method. Or the at least one processor 52 can execute the one or more programs 53 to accomplish the functions of the modules of the exemplary device.

The one or more programs 53 can be divided into one or more modules/units. The one or more modules/units can be stored in the storage unit 51 and executed by the at least one processor 52 to accomplish the disclosed purpose. The one or more modules/units can be a series of program command segments which can perform specific functions, and the command segment is configured to describe the execution process of the one or more programs 53 in the monitoring electronic device 5. For example, the one or more programs 53 can be divided into modules as shown in the FIG. 2, the functions of each module are as described above.

The monitoring electronic device 5 can be any suitable electronic device, for example, a personal computer, a tablet computer, a mobile phone, a PDA, or the like. A person skilled in the art knows that the device in FIG. 5 is only an example and is not to be considered as limiting of the monitoring electronic device 5, another monitoring electronic device 5 may include more or fewer parts than the diagram, or may combine certain parts, or include different parts, such as more buses, and so on.

The at least one processor 52 can be one or more central processing units, or it can be one or more other universal processors, digital signal processors, application specific integrated circuits, field-programmable gate arrays, or other programmable logic devices, discrete gate or transistor logic, discrete hardware components, and so on. The at least one processor 52 can be a microprocessor or the at least one processor 52 can be any regular processor or the like. The at least one processor 52 can be a control center of the monitoring electronic device 5, using a variety of interfaces and lines to connect various parts of the entire monitoring electronic device 5.

The storage unit 51 stores the one or more programs 53 and/or modules/units. The at least one processor 52 can run or execute the one or more programs and/or modules/units stored in the storage unit 51, call out the data stored in the storage unit 51 and accomplish the various functions of the monitoring electronic device 5. The storage unit 51 may include a program area and a data area. The program area can store an operating system, and applications that are required for the at least one function, such as sound or image playback features, and so on. The data area can store data created according to the use of the monitoring electronic device 5, such as audio data, and so on. In addition, the storage unit 51 can include a non-transitory storage medium, such as hard disk, memory, plug-in hard disk, smart media card, secure digital, flash card, at least one disk storage device, flash memory, or another non-transitory storage medium.

If the integrated module/unit of the monitoring electronic device 5 is implemented in the form of or by means of a software functional unit and is sold or used as an independent product, all parts of the integrated module/unit of the monitoring electronic device 5 may be stored in a computer-readable storage medium. The monitoring electronic device 5 can use one or more programs to control the related hardware to accomplish all parts of the method of this disclosure. The one or more programs can be stored in a computer-readable storage medium. The one or more programs can apply the exemplary method when executed by the at least one processor. The one or more stored programs can include program code. The program code can be in the form of source code, object code, executable code file, or in some intermediate form. The computer-readable storage medium may include any entity or device capable of recording and carrying the program codes, recording media, USB flash disk, mobile hard disk, disk, computer-readable storage medium, and read-only memory.

Figure 6:
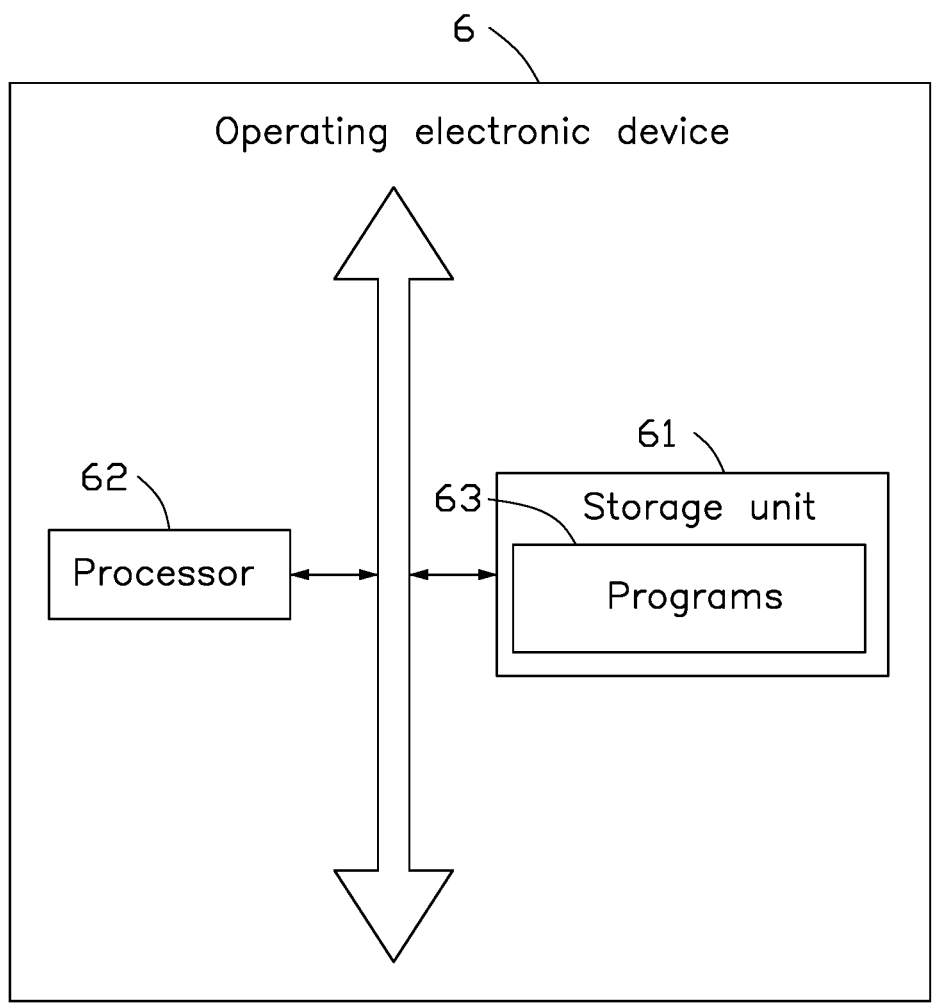
FIG. 6 illustrates a block diagram of an embodiment of an operating electronic device.

FIG. 6 illustrates a block diagram of an embodiment of an operating electronic device. The operating electronic device 6 can include a storage unit 61, at least one processor 62, and one or more programs 63 stored in the storage unit 61 which can be run on the at least one processor 62. The at least one processor 62 can execute the one or more programs 63 to accomplish the steps of the exemplary method. Or the at least one processor 62 can execute the one or more programs 63 to accomplish the functions of the modules of the exemplary device.

The one or more programs 63 can be divided into one or more modules/units. The one or more modules/units can be stored in the storage unit 61 and executed by the at least one processor 62 to accomplish the disclosed purpose. The one or more modules/units can be a series of program command segments which can perform specific functions, and the command segment is configured to describe the execution process of the one or more programs 63 in the operating electronic device 6. For example, the one or more programs 63 can be divided into modules as shown in the FIG. 3, the functions of each module are as described above.

The operating electronic device 6 can be any suitable electronic device, for example, a personal computer, a tablet computer, a mobile phone, a PDA, or the like. A person skilled in the art knows that the device in FIG. 6 is only an example and is not to be considered as limiting of the operating electronic device 6, another operating electronic device 6 may include more or fewer parts than the diagram, or may combine certain parts, or include different parts, such as more buses, and so on.

The at least one processor 62 can be one or more central processing units, or it can be one or more other universal processors, digital signal processors, application specific integrated circuits, field-programmable gate arrays, or other programmable logic devices, discrete gate or transistor logic, discrete hardware components, and so on. The at least one processor 62 can be a microprocessor or the at least one processor 62 can be any regular processor or the like. The at least one processor 62 can be a control center of the operating electronic device 6, using a variety of interfaces and lines to connect various parts of the entire operating electronic device 6.

The storage unit 61 stores the one or more programs 63 and/or modules/units. The at least one processor 62 can run or execute the one or more programs and/or modules/units stored in the storage unit 61, call out the data stored in the storage unit 61 and accomplish the various functions of the operating electronic device 6. The storage unit 61 may include a program area and a data area. The program area can store an operating system, and applications that are required for the at least one function, such as sound or image playback features, and so on. The data area can store data created according to the use of the operating electronic device 6, such as audio data, and so on. In addition, the storage unit 61 can include a non-transitory storage medium, such as hard disk, memory, plug-in hard disk, smart media card, secure digital, flash card, at least one disk storage device, flash memory, or another non-transitory storage medium.

If the integrated module/unit of the operating electronic device 6 is implemented in the form of or by means of a software functional unit and is sold or used as an independent product, all parts of the integrated module/unit of the operating electronic device 6 may be stored in a computer-readable storage medium. The operating electronic device 6 can use one or more programs to control the related hardware to accomplish all parts of the method of this disclosure. The one or more programs can be stored in a computer-readable storage medium. The one or more programs can apply the exemplary method when executed by the at least one processor. The one or more stored programs can include program code. The program code can be in the form of source code, object code, executable code file, or in some intermediate form. The computer-readable storage medium may include any entity or device capable of recording and carrying the program codes, recording media, USB flash disk, mobile hard disk, disk, computer-readable storage medium, and read-only memory.

It should be emphasized that the above-described embodiments of the present disclosure, including any particular embodiments, are merely possible examples of implementations, set forth for a clear understanding of the principles of the disclosure. Many variations and modifications can be made to the above-described embodiment(s) of the disclosure without departing substantially from the spirit and principles of the disclosure. All such modifications and variations are intended to be included herein within the scope of this disclosure and protected by the following claims.

What is claimed is:

1. A field surveying and regulating system comprising:
at least one monitoring electronic device providing monitoring on site for at least one manager, the at least one monitoring electronic device is configured to:
provide for the manager to add at least one project and information as to at least one spot, and to edit the at least one project and the at least one spot information on an online map;
provide for the manager to assign at least one soil drill and at least one drill operator for each of the projects and each of the spots;
provide information for the manager to view regarding drill position of the soil done by each of the soil drills, information as to drill depth done by each of the soil drills, drill time spent sampling done by each of the soil drills, actual work done by each of the soil drills, and at least one photo of actual drill-sampling done by each of the soil drills;
at least one operating electronic device communicating with at least one monitoring electronic device, the at least one operating electronic device providing project information and spot information to the drill operators on site, as assigned by the manager, the at least one operating electronic device is configured to:
provide a view for the drill operator of the project information of the projects of the online map and the spot information of the spots of the online map on the online map to determine information as to drilling for samples for each of the soil drills, each of the soil drills comprising a real-time Kinematic measuring machine;
receive return information returned from the real-time Kinematic measuring machine, the return information comprising the drill position of the soil done by each of the soil drills, the information as to drill depth done by each of the soil drills, and the drill time spent sampling done by each of the soil drills;
receive input actual work done by each of the soil drills, and at least one input photo of actual drill-sampling done by each of the soil drills;
transmit the returned drill position of the soil done by each of the soil drills, the returned information as to drill depth done by each of the soil drills, the returned drill time spent sampling done by each of the soil drills, the input actual work done by each of the soil drills, and the input photo of actual drill-sampling done by each of the soil drills to the at least one monitoring electronic device;
wherein the at least one monitoring electronic device is further configured to:
provide for the at least one manager to edit the project information of the projects; the project information comprising the project name, the sampling date of each of the soil drills, the ID and information of each of the drill operators, the information of each of the soil drills, the sampling method of each of the soil drills, and the time spent information of sampling by each of the soil drills;
add at least one soil drill, cancel at least one soil drill, edit types and descriptions of at least one soil drill, and edit work state of at least one soil drill for each of the projects and each of the spots;
add at least one drill operator for each of the projects, delete at least one drill operator for each of the projects, and edit names of at least one drill operator for each of the projects and each of the spots;

control the online map to track the soil drill and switch screen to display a latitude and longitude of the soil drill and a current depth of the soil drill in real time when performing a sampling process.

2. The system according to claim 1, wherein the at least one monitoring electronic device is further configured to:

provide the online map;

provide an address-searching option for operating, provide a project input interface in response to a selection operation on the address-searching option, and receive a first address information input in the project input interface to provide for the manager to add the project on the online map; each of the projects being displayed on the online map with a first mark.

3. The system according to claim 2, wherein the at least one monitoring electronic device is further configured to:

provide a project interface for inputting a project name, a sampling date of each of the soil drills, information of each of the drill operators, information of each of the soil drills, and a sampling method of each of the soil drills.

4. The system according to claim 2, wherein the at least one monitoring electronic device is further configured to:

provide a first spot adding option for operating, receive a selection operation on the first spot adding option, and receive at least one selection operation on the online map to add at least one spot on the online map, each of the spots being displayed on the online map with a second mark, the second mark being different from the first mark.

5. The system according to claim 1, wherein the at least one monitoring electronic device is further configured to:

provide a project adding option, receive a selection operation on the project adding option, and receive a selection operation on the online map to add the project on the online map.

6. A field surveying and regulating method applied on at least one monitoring electronic device and at least one operating electronic device, the at least one monitoring electronic device communicating with the at least one operating electronic device, the method comprising:

the at least one monitoring electronic device providing for at least one manager to add at least one project and information as to at least one spot, and to edit the at least one project and the at least one spot information on an online map;

the at least one monitoring electronic device providing for at least one manager to assign at least one soil drill and at least one drill operator for each of the projects and each of the spots;

the at least one operating electronic device providing a view for at least one drill operator of the project information of the projects of the online map and the spot information of the spots of the online map on the online map to determine information as to drilling for samples for each of the soil drills, each of the soil drills comprising a real-time Kinematic measuring machine;

the at least one operating electronic device receiving return information returned from the real-time Kinematic measuring machine, the return information comprising the drill position of the soil done by each of the soil drills, the information as to drill depth done by each of the soil drills, and the drill time spent of sampling done by each of the soil drills;

the at least one operating electronic device receiving input actual work done by each of the soil drills, and at least one input photo of actual drill-sampling done by each of the soil drills;

the at least one operating electronic device transmit the returned drill position of the soil done by each of the soil drills, the returned information as to drill depth done by each of the soil drills, the returned drill time spent sampling done by each of the soil drills, the input actual work done by each of the soil drills, and the input photo of actual drill-sampling done by each of the soil drills to the at least one monitoring electronic device;

the at least one monitoring electronic device providing information for the at least one manager to view regarding the drill position of the soil done by each of the soil drills, the information as to drill depth done by each of the soil drills, the drill time spent sampling done by each of the soil drills, the actual work done by each of the soil drills, and the at least one photo of actual drill-sampling done by each of the soil drills;

the method further comprising:

the at least one monitoring electronic device providing for the at least one manager to edit the project information of the projects; the project information comprising the project name, the sampling date of each of the soil drills, the ID and information of each of the drill operators, the information of each of the soil drills, the sampling method of each of the soil drills, and the time spent information of sampling by each of the soil drills;

the at least one monitoring electronic device adding at least one soil drill, cancelling at least one soil drill, editing types and descriptions of at least one soil drill, and editing work state of at least one soil drill for each of the projects and each of the spots;

the at least one monitoring electronic device adding at least one drill operator for each of the projects, deleting at least one drill operator for each of the projects, and editing names of at least one drill operator for each of the projects and each of the spots;

the at least one operating electronic device controlling the online map to track the soil drill and switch screen to display a latitude and longitude of the soil drill and a current depth of the soil drill in real time when performing a sampling process.

7. The method according to claim 6, the method further comprising:

the at least one monitoring electronic device providing the online map;

the at least one monitoring electronic device providing an address-searching option for operating, providing a project input interface in response to a selection operation on the address-searching option, and receiving a first address information input in the project input interface to provide for the manager to add the project on the online map;

each of the projects being displayed on the online map with a first mark.

8. The method according to claim 7, the method further comprising:

the at least one monitoring electronic device providing a project interface for inputting a project name, a sampling date of each of the soil drills, information of each of the drill operators, information of each of the soil drills, and a sampling method of each of the soil drills.

9. The method according to claim 7, the method further comprising:

the at least one monitoring electronic device providing a first spot adding option for operating, receiving a selection operation on the first spot adding option, and receiving at least one selection operation on the online map to add at least one spot on the online map, each of the spots being displayed on the online map with a second mark, the second mark being different from the first mark.

10. The method according to claim 6, the method further comprising:
the at least one monitoring electronic device providing a project adding option, receiving a selection operation on the project adding option, and receiving a selection operation on the online map to add the project on the online map.

11. A field surveying and regulating method applied on at least one monitoring electronic device, the method comprising:
providing for at least one manager to add at least one project and information as to at least one spot, and to edit the at least one project and the at least one spot information on an online map;
providing for at least one manager to assign at least one soil drill and at least one drill operator for each of the projects and each of the spots;
providing information for the at least one manager to view regarding drill position of the soil done by each of the soil drills, information as to drill depth done by each of the soil drills, drill time spent sampling done by each of the soil drills, actual work done by each of the soil drills, and at least one photo of actual drill-sampling done by each of the soil drills;
the method further comprising:
providing for the at least one manager to edit the project information of the projects;
the project information comprising the project name, the sampling date of each of the soil drills, the ID and information of each of the drill operators, the information of each of the soil drills, the sampling method of each of the soil drills, and the time spent information of sampling by each of the soil drills;
adding at least one soil drill, cancelling at least one soil drill, editing types and descriptions of at least one soil drill, and editing work state of at least one soil drill for each of the projects and each of the spots;
adding at least one drill operator for each of the projects, deleting at least one drill operator for each of the projects, and editing names of at least one drill operator for each of the projects and each of the spots;
controlling the online map to track the soil drill and switch screen to display a latitude and longitude of the soil drill and a current depth of the soil drill in real time when performing a sampling process.

12. The method according to claim 11, the method further comprising:
providing the online map;
providing an address-searching option for operating, providing a project input interface in response to a selection operation on the address-searching option, and receiving a first address information input in the project input interface to provide for the manager to add the project on the online map; each of the projects being displayed on the online map with a first mark.

13. The method according to claim 12, the method further comprising:
providing a project interface for inputting a project name, a sampling date of each of the soil drills, information of each of the drill operators, information of each of the soil drills, and a sampling method of each of the soil drills.

14. The method according to claim 13, the method further comprising:
providing a first spot adding option for operating, receiving a selection operation on the first spot adding option, and receiving at least one selection operation on the online map to add at least one spot on the online map, each of the spots being displayed on the online map with a second mark, the second mark being different from the first mark.

15. The method according to claim 11, the method further comprising:
providing a project adding option, receiving a selection operation on the project adding option, and receiving a selection operation on the online map to add the project on the online map.

* * * * *